United States Patent
Johansson et al.

(10) Patent No.: US 6,500,412 B1
(45) Date of Patent: Dec. 31, 2002

(54) CLEAR ANTIPERSPIRANT WITH ALCOHOL FREE ACTIVE

(75) Inventors: Marie Johansson, Watchung, NJ (US); John Brahms, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/117,900

(22) Filed: Apr. 8, 2002

(51) Int. Cl.⁷ .............................. A61K 7/32; A61K 7/00
(52) U.S. Cl. ..................... 424/65; 424/400; 424/401; 514/937; 514/938
(58) Field of Search ................. 424/65, 400, 401; 514/937, 938

(56) References Cited

U.S. PATENT DOCUMENTS

| | | |
|---|---|---|
| 5,162,378 A | 11/1992 | Guthauser |
| 5,587,153 A | 12/1996 | Angelone, Jr. et al. |
| 5,730,963 A | 3/1998 | Hilliard, Jr. et al. |
| 5,863,525 A | 1/1999 | Angelone, Jr. et al. |
| 5,925,338 A | 7/1999 | Karassik et al. |
| 6,007,799 A | 12/1999 | Lee et al. |
| 6,375,937 B1 | 10/2000 | Chopra et al. ................. 424/65 |

FOREIGN PATENT DOCUMENTS

| | | |
|---|---|---|
| EP | 0512770 B1 | 10/1996 |
| WO | WO 92/19221 | 11/1992 |
| WO | WO 01/85118 | 11/2001 |
| WO | WO 01/85121 | 11/2001 |

*Primary Examiner*—Shelley A. Dodson
(74) *Attorney, Agent, or Firm*—Rosemary M. Miano

(57) ABSTRACT

A non-sticky, clear water-in-oil emulsion comprising: (a) 65–90 weight % of an internal phase comprising 5–35 weight % of an antiperspirant salt (anhydrous basis) having a metal:chloride ratio in the range of 0.9–1.4:1; 5–15 weight % of tripropylene glycol; and 35–70 weight % water; and (b) 10–35 weight % of an external phase comprising 1–40 weight % of a volatile silicone which is not an elastomer; 0.1–5 weight % of a silicone copolyol surfactant; and 0–20 weight % of a nonvolatile silicone which is not an elastomer; wherein the composition is free of (1) C1–5 saturated alcohols, (2) added propylene glycol, (3) elastomer gelling agents, (4) soap gelling agents (5) borate gelling agents, and (6) coupling agents, and wherein all amounts are in % by weight based on the total weight of the composition.

13 Claims, No Drawings

CLEAR ANTIPERSPIRANT WITH ALCOHOL FREE ACTIVE

FIELD OF THE INVENTION

This invention relates to an improved efficacy antiperspirant gel with improved aesthetics, especially reduced tack or stickiness. The invention is a compressed water-in-oil emulsion comprising 65–90 weight % of an internal/dispersed active phase which (1) includes an antiperspirant active with a low metal:chloride ratio, (2) is free of added ethanol and propylene glycol, and (3) is free of elastomer, soap and borate gelling agents.

BACKGROUND OF THE INVENTION

U.S. Pat. No. 6,007,799 to Lee et al describes a clear cosmetic gel which is a water-in-oil emulsion and which can include propylene and/or tripropylene glycol. The composition also includes an alkoxylated alkyl substituted siloxane surface active agent.

U.S. Pat. Nos. 5,587,153 and 5,863,525 to Angelone et al describes a clear gel-type cosmetic products which may be made with ethanol and propylene glycol.

U.S. Pat. No. 5,925,338 to Karassik et al describes clear antiperspirant or deodorant gel compositions with linear silicone to reduce staining which comprises a polyether substituted silicone emulsifying agent and a volatile cyclic silicone and a volatile linear silicone.

U.S. Pat. No. 5,730,963 to Hilliard describes a cosmetic gel having low irritation wherein the glycol component is controlled as to composition. Selected embodiments include those with tripropylene glycol and others having no added propylene glycol.

U.S. Pat. No. 5,393,518 to Kwass describes an optically clear liquid antiperspirant product with is a stable water-in-oil emulsion having a viscosity of less than 1000 cps. The composition includes the use of propylene glycol and ethanol.

WO 01/85118 to Unilever describes antiperspirant/deodorant compositions which are free of "simple glycols" (as defined) and middle chain alcohols.

WO 01/85121 to Unilever is similar to WO 01/85118 but also includes a coupling agent and an ethylene glycol adduct.

SUMMARY OF THE INVENTION

The invention comprises a clear, low tack, water-in-oil emulsion comprising:
(a) 5–25 weight % (preferably 10–25% and more preferably 15–25%) of an antiperspirant salt (anhydrous basis) having a metal:chloride ratio in the range of 0.9–1.4:1;
(b) 5–15 weight % of tripropylene glycol;
(c) 35–70 weight % water;
(d) 5–30 weight % of a volatile silicone which is not an elastomer;
(e) 0.1–5 weight % (particularly 0.1–3% and more particularly 0.1–1.0%) of a silicone copolyol surfactant; and
(f) 0–20 weight % (particularly 1–15%, and more particularly 1–9%) of a nonvolatile silicone which is not an elastomer;
having an external phase comprised of (a)+(b)+(c) and an internal phase of (d)+(e)+(f), wherein the ratio of external phase to internal phase is in the range of 65–90:10–35 (more particularly 75–85:15–25), and wherein the composition is free of (1) added low molecular weight alcohols (that is, C1–5 saturated alcohols, particularly ethanol), (2) added propylene glycol (no more than 1% and preferably less than 0.1%), (3) elastomer gelling agents, (4) soap gelling agents (5) borate gelling agents, and (6) coupling agents, and wherein all amounts are in % by weight based on the total weight of the composition.

It should be noted that the ability to use tripropylene glycol ("TPG") in this invention is unexpected, since normally glycols cause such compositions to be sticky. In this formulation, the use of TPG does not result in a sticky formulation, as evidenced by sensory testing on skin as described below.

DETAILED DESCRIPTION OF THE INVENTION

For the antiperspirant active used in the internal (also called "active") phase various antiperspirant active materials that can be utilized according to the present invention provided that they are soluble at a suitable concentration in the active phase and have the required metal:chloride ratio. These include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PEG, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein. Particular actives include Westchlor ZR 35B aluminum zirconium tetrachlorhydrex gly(from Westwood Chemical Corporation, Middletown, N.Y.);, and Rezal 36 GP and AZP 902 aluminum zirconium tetrachlorhydrex gly both from Reheis, Berkeley Heights, N.J. as well as Rezal AZZ 908 from Reheis. In general, the metal:chloride mole ratio is in the range of 2.1–0.9:1 for such salts.

Actives of special interest because they form low RI solutions include: Westchlor Zr 35BX4 (30–35% actives in water) from Westwood Chemical Company, Middletown, N.Y.; Summit AZG-368 (28–32% in water) from Summit Research Labs, Huguenot, N.Y.; Summit Z522, Z529, Z498 and Z576; and aluminum chloride (28% in water) which may be obtained from several sources. In general, the metal:chloride mole ratio is approximately 1.2:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1.

Mixtures of actives can also be used, provided a suitable amount of low RI material is used to achieve a satisfactory product.

Antiperspirant actives can be incorporated into compositions according to the present invention in amounts in the range of 7–25% (on an anhydrous solids basis), preferably 7–20%, by weight, of the total weight of the composition. The amount used will depend on the formulation of the composition. At amounts at the higher end of the range (especially in a range of 9–20% or 9–25%, a good antiperspirant effect can be expected. As noted above, the active is preferably included in the compositions of the invention by premixing the active with water.

Tripropylene glycol (2–25 weight %, preferably 5–20%, and more preferably 9–10%) is used in the invention and is of special interest because of (1) its low irritancy and (2) the unexpected lack of tackiness associated with its use as compared with other glycols such as propylene glycol. There is one complication, however, since the antiperspirant active is not as soluble in tripropylene glycol as it is in some of the other choices. It may be advantageous to include a small amount of other selected glycols to give the desired balance between irritancy and solubility for the antiperspirant active. These selected glycols which may be included in the compositions of this invention are selected from the group consisting of diethylene glycol, triethylene glycol, tetraethylene glycol, dipropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

More particular examples of the glycol component include one or more members of the group consisting of dipropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Mixtures of glycols may be used to balance these desirable properties.

The compositions of the invention are free of added propylene glycol, however, it is understood that small amounts of propylene glycol may be present as impurities in commercial grades of certain glycols such as tripropylene glycol. For the formulations of this invention, the amount of propylene glycol must not exceed 1 weight %, is preferably less than 0.1 weight % and ideally is zero.

The level of water is necessarily dependent other factors including the need to accommodate other ingredients in the internal phase while retaining a refractive index which yields a clear formula. It is anticipated that other than antiperspirant active, tripropylene glycol and optional ingredients, the remainder of the internal phase will be water.

For the external phase, also called the oil phase the following ingredients may be used.

For the volatile silicone component, an amount of 1–40 weight % may be used; this includes the incremental amount needed to complete the selected amount of the external phase (quantum sufficient or "q.s."). Particular ranges include 2–30%, (more particularly 3–20% and, even more particularly, 5–10%) by weight based on the entire weight of the composition which may be used. By volatile silicone material is meant a material that has a measurable vapor pressure at ambient temperature. For the volatile silicone portion, examples of volatile silicones (particularly silicones with a boiling point of 250 degrees C or less at atmospheric pressure) include cyclomethicone (especially cyclopentasiloxane, also called "D5"), "hexamethyldisiloxane", and low viscosity dimethicone (for example, Dow Corning® 200 fluid having a viscosity of 1–200 centistokes). Such volatile silicones include conventional cyclic and linear volatile silicones Illustratively, and not by way of limitation, the volatile silicones are one or more members selected from the group consisting of cyclic polydimethylsiloxanes such as those represented by Formula III:

Formula III

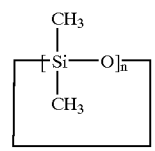

where n is an integer with a value of 3–7, particularly 5–6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members selected from the group consisting of linear polydimethylsiloxanes such as those represented by Formula IV:

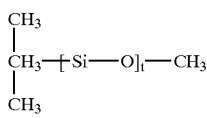

Formula IV and t is selected to obtain a viscosity of 1–200 centistokes.

The alkoxylated, alkyl substituted siloxane surface active agent is preferably, but not limited to, a dimethicone copolyol. An illustrative alkoxylated silicone-containing surfactant utilizable according to the present invention is cetyl dimethicone copolyol, referred to in U.S. Pat. No. 5,162,378 to Guthauser. Illustratively, the alkoxylated, alkyl substituted siloxane surface active agent is included in the composition in an amount of 0.2–2.0 weight %, based on the total weight of the composition.

A specific cyclomethicone-dimethicone copolyol fluid which can be utilized to provide the alkoxylated silicone-containing surface active agent is a mixture of cyclomethicone and dimethicone copolyol designated as DC3225C from Dow Corning Corp. This is a polyether substituted silicone of cyclomethicone and dimethicone copolyol (refractive index (RI)=1.3994). This DC 3225C, which is an emulsifying agent, is useful for preparing stable water-in-oil emulsions where a silicone makes up a large portion of the oil phase, and is a dispersion of a silicone surfactant (dimethicone copolyol) (10% by weight) in cyclomethicone (Dow Corning 344 Fluid) (90% by weight).

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The lower concentration materials such as DOW CORNING® 5225C material is of particular interest.

In one particular embodiment 0.1–5% (particularly 0.5–5.0%) of a 10–50% silicone copolyol such as dimethicone copolyol in cyclomethicone mixture may be used, wherein the amount of mixture added is selected so that the level of silicone copolyol in the cosmetic composition is in the range of 0.25–5.0% (particularly 1%) (for example, 0.25–10% of a 40%–50% dimethicone copolyol in cyclomethicone mixture).

The formula may optionally contain one or more of the following non-volatile silicones or combinations there of: (0–20%, more preferably 1–15%, more preferably 1–9%) of a non-cross-linked linear or branched polyalkylsiloxanes, polyalkyarylsiloxanes, polyestersiloxanes, polyethersiloxane copolymers, polyfluorosiloxanes, polyaminosiloxanes, with a mean molecular weight of at least 1000. For instance the linear organo-substituted polysiloxanes which are polymers of silicon/oxygen with general structure:

(1) $(R^{20})_3SiO(Si(R^{21})_2O)_xSi(R^{22})_3$ where $R^{20}$, $R^{21}$ and $R^{22}$ can be the same or different and are each independently selected from the group consisting of phenyl and C1–C60 alkyl; or (2) $HO-(R^{24})_2-SiO-(Si(R^{25})_2O)_xSi(R^{26})_2-OH$, where $R^{24}$, $R^{25}$ and $R^{26}$ can be the same or different and are each independently selected from the group consisting of phenyl and C1–C60 alkyl; or (3) organo substituted silicon compounds of formula $R^{27}-Si(R^{28})O-Si-R^{29}$ which are not polymeric where $R^{27}$, $R^{28}$ and $R^{29}$ can be the same or different and are each independently selected from the group consisting of phenyl and C1–C60 alkyl optionally with one or both of the terminal R groups also containing an hydroxyl group. Specific examples include dimethicone, dimethiconol behenate, $C_{30-45}$ alkyl methicone, stearoxytrimethylsilane, phenyl trimethicone and stearyl dimethicone.

Specific examples include dimethicone, dimethiconol behenate, $C_{30-45}$ alkyl methicone, stearoxytrimethylsilane, phenyl trimethicone, stearyl dimethicone and dimethiconol.

Other optional ingredients may also be added as desired. Optional ingredients may be incorporated into the internal or external phase as appropriate. These include (but are not limited to) a salt (especially NaCl), coloring agents and the following:

(1) A deodorant active—Effective amounts of antimicrobial agents, for example, 0.05–5.0 percent (particularly 0.1–1% and, more particularly, 0.25–1.0%) by weight based on the total weight of the composition; examples include bacteriostatic quaternary ammonium compounds (such as cetyl trimethyl-ammonium bromide, and cetyl pyridinium chloride), 2,4,4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™ SC 50) and various zinc salts (for example, zinc ricinoleate). Triclosan or Triclocarban can, illustratively, be included in an amount of from 0.05% to about 0.5% by weight, of the total weight of the composition.

(2) fragrance—0–5%, more preferably 0.05–1.5%, more preferably 0.5–1%, especially a mixture of volatile organic compounds which impart a pleasant odor to the product and mask the base odor of the product formulation, if any. It is assumed that fragrances may impart other benefits to the consumer such as underarm malodor masking bacteriostatic effect. Fragrances consist of complex mixtures of volatile organic compounds and natural essential oils including but not limited to those skilled in the art. Examples of fragrance materials commonly used the formulations disclosed in this invention include but are not limited to those described in "Perfume and Flavor Chemicals" by Steffan Arctander Allured Publishing Co., Carol Stream, Ill, 2000.

(3) emollient—The emollient or emollient mixture or blend thereof incorporated in compositions according to the present invention can, illustratively, be included in amounts of 0.5–50%, preferably 1–25%, more preferably 1–5%, by weight, of the total weight of the composition. Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

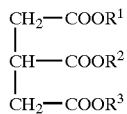

Formula VI wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO—OR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated alcohols (including guerbet alcohols) with general structure $R^7OH$ where $R^7$ can be C7–C30 saturated or unsaturated, straight chained or branched hydrocarbon. Specific examples for the hydrocarbon portion include, lauryl, myristyl, cetyl, isocetyl, stearyl, isostearyl, oleyl, ricinoleyl and erucyl alcohol;

(e) lanolin and its derivatives which are a complex esterified mixture of high molecular weight esters of (hydroxylated) fatty acids with aliphatic and alicyclic alcohols and sterols. General structures would include $R^8CH_2—(OCH_2CH_2)_nOH$ where $R^8$ represents the fatty groups derived from lanolin and n=5 to 75 or $R^9CO—(OCH_2CH_2)_nOH$ where $R^9CO—$ represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(f) alkoxylated alcohols wherein the alcohol portion is selected from aliphatic alcohols having 2–18 carbons and more particularly 4–18 carbons, and the alkylene portion is selected from the group consisting of ethylene oxide, and propylene oxide having a number of alkylene oxide units from 2–53 and, more particularly, from 2–15. Examples include cetyl glyceryl ether; isostearyl glyceryl ether; isostearyl glyceryl pentaerythrityl ether; laureth-5 butyl ether; oleyl glyceryl ether; PEG-4 ditallow ether; polyglyceryl-3 cetyl ether; polyglyceryl-4 lauryl ether; PPG-9 diglyceryl ether; propylene glycol myristyl ether. More specific examples include PPG-14 butyl ether, PPG-53 butyl ether laureth-5 butyl ether and PEG-4 ditallow ether.

(g) ethers selected from the group consisting of dicaprylyl ether; dicetyl ether; dimethyl ether; distearyl ether; ethyl ether; isopropyl hydroxycetyl ether; methyl hexyl ether; polyvinyl methyl ether; and (j) mixtures and blends of two or more of the foregoing.

Particular examples of suitable emollients include members of the group consisting of Octyloxyglyderin (SENSIVA SC50 from Schiülke Mayr, Norderstedt, Germany) (which can be used as an emollient as well as an antibacterial); Polysorbate 80 (TWEEN 80 from ICI Americas, Wilmington, Del.); Oleth-20; ethoxylated alcohols such as steareth-2, nonoxynol-2, PPG-4-Ceteth-1; ethoxylated carboxylic acids such as PEG-4 dilaurate, PEG-2 oleate; glyceryl esters such as PEG-2 castor oil, polyglyceryl-3 oleate, glyceryl stearate; sorbitan derivatives such as sorbitan oleate; PPG-3 myristyl ether (such as WITCONOL APM from Goldschmidt), a dimethiconol (such as Dow Corning® DC1501 dimethiconol), neopentyl glycol diheptanoate, PEG-8 laurate, isocetyl stearate, dimethicone copolyol laurate, Dow Corning 2501 cosmetic wax (dimethicone copolyol); isostearyl isostearate, isostearyl palmitate, isostearyl alcohol, PPG-5-ceteth-20, PPG-10-cetyl ether, triethyl hexanoin, ethyl hexyl isostearate, glyceryl oleate, and isopropyl isostearate.

(5) co-surfactant—0–5% (preferably 0–3%, and more preferably 0–1%) of a co-surfactant (which can also be a mixture or blend of surfactants) which is at least one member selected from the group consisting of:

(a) sorbitan esters and ethoxylated sorbitan esters (for example PEG-20 sorbitan isostearate, sorbitan monolaurate, polysorbate-20, polysorbate-40, polysorbate-60, polysorbate-80);

(b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, and Oleath-20);

(c) ethoxylated adducts (for example, PEG-25 stearate, glyceryl stearate and PEG-100 stearate);

(d) PEG esters (for example, PEG-8 oleate, PEG-8 laurate, PEG-8 dilaurate, PEG-12 dilaurate, PEG-80 diisostearate, PEG-40 stearate);

(e) propoxylates (for example, PPG-10 butanediol, PPG-50 oleyl ether, PPG-2-ceteareth-9, PPG-3-deceth-3, PPG-5-ceteth-20);

(f) ethoxylated modified triglycerides (for example, PEG-20 corn glycerides, PEG-12 palm kernel glycerides); and (g) block copolymers which are alkoxylated glycols having ethoxylated and propoxylated segments (for example, Poloxamers 182 and 234, and Meroxapol 174);

wherein the co-surfactant is selected so that it has an HLB (hydrophilic-lipophilic balance) value in the range of 1–15, preferably $\leqq 8$.

The HLB parameter is a well known parameter the calculation of which is disclosed and explained in numerous references. For nonionic surfactants, data obtained by actual analysis is usually a more accurate measure of HLB values (rather than theoretical determinations). For purposes of this invention it is intended that either the actual or theoretical HLB value may be used as the basis for selection.

For the co-surfactant having an HLB value $\leq 8$, examples include:

(a) ethoxylated alcohols such as steareth-2, Oleth-3, nonoxynol-2, PPG-4-Ceteth-1;

(b) ethoxylated carboxylic acids such as PEG-4 dilaurate, PEG-2 oleate;

(c) glyceryl esters such as PEG-2 castor oil, PEG-7 hydrogenated castor oil, glyceryl monooleate, glyceryl monostearate, triglycerol monooleate, decaglyceryl tetraoleate, and polyglyceryl-3 oleate, glyceryl stearate;

(d) sorbitan derivatives such as sorbitan oleate, sorbitan monostearate, sorbitan tristearate, sorbitan monooleate, sorbitol trioleate, sorbitan monotallate, sorbitan isostearate;

(e) sugar esters such as sucrose distearate; and (f) lanolin alcohol.

The surfactant or blend of surfactants incorporated into the compositions of the present invention can, illustratively, be included in amounts of 0.1–10%, preferably 0.3–5%, and more preferably 0.5–1.5%, by weight based on the total weight of the composition. This surfactant portion includes both the silicone copolyol and the co-surfactant.

If salt is used, the amount used may be in the range of 0–5%, preferably 0.1–4% and, more preferably, 0.5–2% by weight based on the total weight of the composition. Examples of suitable salts include NaCl (most commonly used), $CaCl_2$, KCl, and $ZnCl_2$.

Sensates (ingredients that provide unique skin sensations such as warmth, cooling, tingling, etc.) may also be added. These include but are not limited to methyl salicylate, menthol, menthol derivatives, capsaicin, or benzocaine.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C unless otherwise indicated. If alcohol is used, it is 95% unless otherwise indicated. Unless otherwise indicated, "water" or "D.I. water" mean deionized water. As is true throughout the application, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). Viscosities are measured using Brookfield viscometers unless otherwise indicated. While specific amounts of particular elastomers have been described, there are chemical differences in the variety of elastomers that are available. The use of different elastomers may result in the need to increase or decrease the amount of elastomer used in a particular formulation, especially if a clear product is desired.

Example 1

General Method

In general, the external and internal phases are formed separately either at room temperature or with heating as described below. The internal phase is added to the external phase very slowly while stirring vigorously to form an emulsion. After the addition of the internal phase is completed, the emulsion is stirred at high speed for an additional 10 minutes to achieve a homogeneous mixture. The desired high viscosity of the emulsion is achieved by homogenizing the emulsion using either batch or continuing process conditions. The fragrance can be added at any time prior to the final homogenization step.

Preparation of the external phase:

The ingredients to be used in the external phase are weighed out at room temperature and combined in a suitable vessel such as a 600 milliliter plastic beaker. All the ingredients are added and the mixture is stirred at approximately 500 rpm for 10 minutes using an overhead mixer such as Eurostar equipment from IKA Labortechnik.

Preparation of the internal phase:

The ingredients to be used in the internal phase are weighed out at room temperature and combined in a suitable vessel such as a 600 milliliter plastic beaker. The mixture is stirred for a time sufficient to achieve homogeneity.

Preparation of the emulsion:

The internal phase made as described above is then added to the external phase over the course of 10 minutes while stirring at a speed of 700–900 rpm. The initial addition should be dropwise and then in a slow stream. After completion of the addition, the emulsion is mixed at 1300 rpm for 10 minutes using an overhead mixer such as the Eurostar equipment described previously, and then homogenized for 1–3 minutes using a homogenizer (for example, a Gilford-Wood Model 1-L from Greerco Corp., (Hudson, N.H.)) at a reading of about 70 on a Powerstat Variable Autotransformer from Superior Electric Co. (Bristol, Conn.).

The fragrance (if any is used) is added last and may be added to the external phase normally (although it may be added to either the external phase or the internal phase) or the final formula prior to homogenization.

If a co-surfactant is included it is added to the external phase prior to final mixing. Mixing time can be extended to yield a homogeneous solution. If a co-surfactant is a solid, it should be melted on a hotplate before adding it to the external phase. The oil phase is then mixed until it is homogeneous. The active phase is then added to the oil phase as described above.

If a salt solution is included, the salt water is prepared by dissolving the crystalline salt in water and stirring until dissolved. The salt water solution is then added to the rest of the internal phase and the mixture is stirred until homogeneous. The rest of the procedure is then followed to create the emulsion.

Further Processing:

The product is then further processed by homogenization to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Conn.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200–30 both available from Sonic Corporation of Stratford, Conn. Process conditions are chosen to give the desired final product viscosity.

Examples 2–7

For Examples 2–7, the method of Example 1 may be repeated with the amounts of ingredients listed in Table A. Batches may be made in 400 gram amounts. "RI" stands for refractive index.

TABLE A

| Ingredient | Ex. 2 | Ex. 3 | Ex. 4 | Ex. 5 | Ex. 6 | Ex. 7 |
|---|---|---|---|---|---|---|
| Part 1 | 18.70 | 18.70 | 18.70 | 18.70 | 18.70 | 18.70 |
| Dimethicone copolyol DC5225C | 9.00 | 9.00 | 9.00 | 9.00 | 9.00 | 9.00 |
| Cyclomethicone | — | 0.05 | 0.25 | — | 0.65 | 0.85 |
| Dimethicone DC200 (50 cps) | 7.25 | 7.25 | 7.25 | 7.25 | 7.25 | 7.25 |
| Phenyltrimethicone | 1.75 | 1.70 | 1.50 | 1.75 | 1.10 | 0.90 |
| Fragrance | 0.70 | 0.70 | 0.70 | 0.70 | 0.70 | 0.70 |
| Part 2 | 81.30 | 81.30 | 81.30 | 81.30 | 81.30 | 81.30 |
| Antiperspirant active Summit Z529 (28% anhydrous) | 67.90 | 67.90 | 67.90 | 71.90 | 71.90 | 71.90 |
| Tripropylene glycol | 13.40 | 13.40 | 13.40 | 9.40 | 9.40 | 9.40 |
| RI Part 1 | 1.4072 | 1.4070 | 1.4063 | 1.4072 | 1.4049 | 1.4042 |
| RI Part 2 | 1.4082 | 1.4082 | 1.4082 | 1.4062 | 1.4062 | 1.4062 |
| RI Total Sample | | | | | | |

Example 5

Evaluation of Stickiness

To judge sensory attributes, a panel of 10 judges that have been screened and trained to evaluate sensory attributes is used. Each judge assigns an integer between 0 and 14, where 0 represents no manifestation of the attribute and 14 is the maximum expression of that attribute. To evaluate stickiness in an underarm product, the product is applied using four strokes in the underarm. Each judge tests two products per session, one in each underarm. The final score is the average score of the judges. Evaluations start at application, time=0, and continue for a predetermined time. Five minutes have been determined to be a relevant time for consumer perception of stickiness. A stickiness score of less than or equal to 0.5, 5 minutes after application is considered to be non-sticky. An average score of ≦0.5 indicates that at least half of the judges rated the stickiness as zero or not perceptible. The results found that a formulation of the invention (Example 5) was judged non-sticky with an average value after 5 minutes of 0.3, while the average value for the Control (a commercially available gel product—Mennen Speedstick Gel Aqua Sport) was slightly over 2 and deemed sticky.

We claim:

1. A clear, low tack, water-in-oil emulsion comprising:
   (a) 5–25 weight % of an antiperspirant salt (anhydrous basis) having a metal:chloride ratio in the range of 0.9–1.4:1;
   (b) 5–15 weight % of tripropylene glycol;
   (c) 35–70 weight % water;
   (d) 5–30 weight % of a volatile silicone which is not an elastomer;
   (e) 0.1–5 weight % of a silicone copolyol surfactant; and
   (f) 0–20 weight % of a nonvolatile silicone which is not an elastomer;
   having an external phase comprised of (a)+(b)+(c) and an internal phase of (d)+(e)+(f), wherein the ratio of external phase to internal phase is in the range of 65–90:10–35, and wherein the composition is free of (1) added low molecular weight alcohols having 1–5 carbons), (2) added propylene glycol, (3) elastomer gelling agents, (4) soap gelling agents (5) borate gelling agents, and (6) coupling agents, and wherein all amounts are in % by weight based on the total weight of the composition.

2. An emulsion according to claim 1 wherein the ratio of external phase to internal phase is in the range of 75–85:15–25.

3. An emulsion according to claim 1 comprising 10–25 weight % of the antiperspirant active.

4. An emulsion according to claim 1 comprising 0.1–3% of the silicone copolyol.

5. An emulsion according to claim 1 comprising 0.1–1.0% of the silicone copolyol.

6. An emulsion according to any one of claims 1, 4 or 5 wherein the silicone copolyol is dimethicone copolyol and the volatile silicone is a cyclomethicone.

7. An emulsion according to claim 1 comprising 1–15% of the nonvolatile silicone.

8. An emulsion according to claim 1 comprising 1–9% of the nonvolatile silicone.

9. An emulsion according to claim 1 or claim 8 wherein the nonvolatile silicone is selected from the group consisting of non-crosslinked linear or branched polyalkylsiloxanes, polyalkylaryl siloxanes, polyestersiloxanes, polyethersiloxane copolymers, polyfluorosiloxanes, and polyaminosiloxanes each having a mean molecular weight of at least 1000.

10. An emulsion according to any one of claims 1, 8 or 9 wherein the nonvolatile silicone is selected from the group consisting of dimethicone, dimethiconol behenate, $C_{30-45}$ alkyl methicone, stearoxytrimethylsilane, phenyl trimethicone, stearyl dimethicone and dimethiconol.

11. An emulsion according to claim 1 additionally comprising at least one member selected from the group consisting of:
   (a) 0.05–5.0 weight % of an antimicrobial agent;
   (b) 0–5 weight % of a fragrance;
   (c) 0–5 weight % of a salt;
   (d) 0.5–50 weight % of an emollient selected from the group consisting of
      (1) fats and oils selected from the group consisting of saturated and unsaturated glyceryl esters of fatty acids or triglycerides of Formula VI:

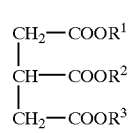

Formula VI wherein each of $R^1$, $R^2$, and $R^3$ may be the same or different and have a carbon chain length of 7 to 30;

(2) hydrocarbons selected from the group consisting of paraffins, petrolatum, hydrogenated polyisobutene, and mineral oil;

(3) esters of formula $R^4CO$—$OR^5$ wherein $R^4$ and $R^5$ are each independently selected from the group consisting of C7–C30 saturated, unsaturated, straight chained and branched hydrocarbons;

(4) saturated and unsaturated alcohols of formula $R^7OH$ where $R^7$ is selected from the group consisting of C7–C30 saturated, unsaturated, straight chained and branched hydrocarbons;

(5) lanolin and its derivatives of formula $R^8CH_2$—$(OCH_2CH_2)_nOH$ where $R^8$ represents the fatty groups derived from lanolin and n=5 to 75 or $R^9CO$—$(OCH_2CH_2)_nOH$ where $R^9CO$— represents the fatty acids derived from lanolin and n=5 to 100;

(6) alkoxylated alcohols wherein the alcohol portion is selected from aliphatic alcohols having 2–18 carbons and the alkylene portion is selected from the group consisting of ethylene oxide, and propylene oxide having a number of alkylene oxide units from 2–53;

(7) ethers selected from the group consisting of dicaprylyl ether; dicetyl ether; dimethyl ether; distearyl ether; ethyl ether; isopropyl hydroxycetyl ether; methyl hexyl ether; polyvinyl methyl ether; and (8) mixtures and blends of two or more of the foregoing;

(e) 0–5 weight % of a co-surfactant which is at least one member selected from the group consisting of:

(A) sorbitan esters and ethoxylated sorbitan esters;

(B) ethoxylates selected from the group consisting of Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, and Oleath-20;

(C) ethoxylated adducts selected from the group consisting of PEG-25 stearate, glyceryl stearate and PEG-100 stearate;

(D) PEG esters selected from the group consisting of PEG-8 oleate, PEG-8 laurate, PEG-8 dilaurate, PEG-12 dilaurate, PEG-80 diisostearate, and PEG-40 stearate;

(E) propoxylates selected from the group consisting of PPG-10 butanediol, PPG-50 oleyl ether, PPG-2-ceteareth-9, PPG-3-deceth-3, and PPG-5-ceteth-20;

(F) ethoxylated modified triglycerides; and (G) block copolymers which are alkoxylated glycols having ethoxylated and propoxylated segments;

wherein the co-surfactant is selected so that it has a hydrophilic-lipophilic balance value in the range of 1–15.

12. The emulsion as claimed in claim 11 wherein the co-surfactant has a hydrophilic-lipophilic balance value $\leq 8$ and is selected from the group consisting of:

(a) ethoxylated alcohols selected from the group consisting of steareth-2, Oleth-3, nonoxynol-2, and PPG-4-Ceteth-1;

(b) ethoxylated carboxylic acids selected from the group consisting of PEG-4 dilaurate, and PEG-2 oleate;

(c) glyceryl esters selected from the group consisting of PEG-2 castor oil, PEG-7 hydrogenated castor oil, glyceryl monooleate, glyceryl monostearate, triglycerol monooleate, decaglyceryl tetraoleate, polyglyceryl-3 oleate, and glyceryl stearate;

(d) sorbitan derivatives selected from the group consisting of sorbitan oleate, sorbitan monostearate, sorbitan tristearate, sorbitan monooleate, sorbitol trioleate, sorbitan monotallate, and sorbitan isostearate;

(e) sucrose distearate; and (f) lanolin alcohol.

13. An emulsion as claimed in claim 1 wherein the antiperspirant salt is an aluminum zirconium tetrachlorohydrex glycine salt having a metal to chloride ratio in the range of 0.9–1.2:1 and a glycine:zirconium mole ratio greater than 1.3:1.

* * * * *